US006593455B2

(12) United States Patent
van der Spoel et al.

(10) Patent No.: US 6,593,455 B2
(45) Date of Patent: Jul. 15, 2003

(54) TRIPEPTIDE AMIDES THAT BLOCK VIRAL INFECTIVITY AND METHODS OF USE THEREOF

(75) Inventors: David van der Spoel, Uppsala (SE); Csaba Hetényi, Uppsala (SE); Ákos Végvári, Uppsala (SE); Stefan Höglund, Uppsala (SE); Jin Su, Toronto (CA); Sarah Sandin-Reneby, Stockholm (SE); Laura Goobar-Larsson, Stockholm (SE); Anders Vahlne, Stockholm (SE)

(73) Assignee: Tripep AB, Huddinge (SE)

( * ) Notice: Subject to any disclaimer, the term of this patent is extended or adjusted under 35 U.S.C. 154(b) by 0 days.

(21) Appl. No.: 09/938,806

(22) Filed: Aug. 24, 2001

(65) Prior Publication Data
US 2003/0060599 A1 Mar. 27, 2003

(51) Int. Cl.[7] .................................................. A61K 5/00
(52) U.S. Cl. ........................ 530/331; 530/332; 530/334; 530/345; 514/2
(58) Field of Search .................... 514/2; 530/331, 530/332, 334, 345

(56) References Cited

U.S. PATENT DOCUMENTS

| | | |
|---|---|---|
| 4,215,112 A | 7/1980 | Goldstein et al. |
| 4,528,133 A | 7/1985 | Kasafirek et al. |
| 4,658,013 A | 4/1987 | Morgan |
| 4,950,647 A | 8/1990 | Robins et al. |
| 5,336,758 A | 8/1994 | Berzofsky et al. |
| 5,346,989 A | 9/1994 | Vahlne et al. |
| 5,449,752 A | 9/1995 | Fujii et al. |
| 5,470,951 A | 11/1995 | Roberts |
| 5,478,810 A | 12/1995 | Stuber et al. |
| 5,571,892 A | 11/1996 | Fujii et al. |
| 5,607,858 A | 3/1997 | Stuber et al. |
| 5,627,035 A | 5/1997 | Vahlne et al. |
| 5,710,128 A | 1/1998 | Fujii et al. |
| 5,770,620 A | 6/1998 | Mjalli et al. |
| 5,776,899 A | 7/1998 | Matsumoto et al. |
| 5,817,626 A | 10/1998 | Findeis et al. |
| 5,830,994 A | 11/1998 | D'Hinterland et al. |
| 5,843,901 A | 12/1998 | Bemis et al. |
| 5,843,904 A | * 12/1998 | Bemis et al. .................. 514/18 |
| 5,843,995 A | 12/1998 | Rana et al. |
| 5,846,714 A | 12/1998 | Haskill et al. |

(List continued on next page.)

FOREIGN PATENT DOCUMENTS

| | | |
|---|---|---|
| EP | 0 421 074 A1 | 4/1991 |
| EP | 0 894 855 A2 | 2/1999 |
| EP | 0 900 566 A1 | 3/1999 |

(List continued on next page.)

OTHER PUBLICATIONS

Abdel–Meguid et al., "An orally bioavaiable HIV–1 protease inhibitor containing an imidazole–derived peptide bond replacement: Crystallographic and pharmacokinetic analysis," *Biochemistry*, 33(39):11671–11677 (1994).

Ashkenazi et al., "Safety and antitumor activity of recombinant soluble Apo2 lignad," *J Clinical Investigation*, 104(2):155–162 (1999).

Durso et al., "The antimitotic tripeptide hemiasterlin," *Pro Am Assoc Cancer Res Annual Meeting*, vol. 40, p. 286, Mar. 1999.

(List continued on next page.)

*Primary Examiner*—Jeffrey Stucker
(74) *Attorney, Agent, or Firm*—Knobbe, Martens, Olson & Bear, LLP

(57) ABSTRACT

Embodiments relate to the discovery that tripeptide amides, which correspond to viral capsid sequences, can be used to inhibit viral infection, including human immunodeficiency virus (HIV) infection. More specifically, medicaments comprising tripeptide amides and methods of using said compounds for the prevention and treatment of viral infection, such as HIV infection, are provided.

5 Claims, 1 Drawing Sheet

| | |
|---|---|
| hIV-1 | SPTS-ILDIKQGPKEPFRDYVDRFYKTLRAEQA—SQEVKNWMTETLLVQNANPDCKTILKALG-PAATLE-EMMTAC—QGVGGPGHK—ARVL// (SEQ. ID NO. 1) |
| HIV-2 | NPTN-ILDIKQGPKEPFQSYVDRFYKSLRAEQT—DPAVKNWMTQTLLIQNANPDCKLVLKGLG—MNPTLEEMLTAC—QGVGGPGQK—ARLM//(SEQ. ID NO 2) |
| SIV | NPVN-ILDIKQGPKEPFQSYVDRFYKSLRAEQA—DPAVKNWMTQTPLIQNANP DCKLVLKGLG—MNPTLEEMLTAC—QGVGGPGQK—ARLM//(SEQ. ID NO.3) |
| HTLV-1 | DPS—WASILQGLEEPYHAFVERLNIALDNGLP—-EGTPKDPILRSLAYSNANKECQKLLQARG—HTNSPLGDMLR AC—Q-TWTPKDK—TKVL—//(SEQ. ID NO. 4) |
| MPMV | DPGASLTGVKQGPDEPFADFVHRLITTAGRIFG—-SAEAGVDYVKQLAYENANPACQAAIRPYR—KKTDLTGYI LC—SDIGPSYQQGLAMA—-//(SEQ. ID NO.5) |
| MMTV | —--LAGLKQGNEESYETFISRLEEAVYRMMP—RGEGSDIL IKQLAWENAN SLCQDLIRPIR—KTGTIQDYI RAC—LDASPAV VQGMAY—//(SEQ. ID NO. 6) |
| MMLV | TN LAKVKGITQGPNESPSAFLERLKEAYRRYTPYDPEDPGQETNVSMSFIWQSA-PDIGRKLERLEDLRNKTL-GDLVREA—ERIFNKRE———//(SEQ. ID NO.7) |
| RSV | EPTDPWADIMQQPSESFVDFANRLIKAVEGSDL—P PSARAPVIIDCFRQKSQPDIQQLIRAAP-STLTTPGEIIKY VLDRQKTAPLTDQGIAAAM//(SEQ ID NO. 8 ) |

MHR

U.S. PATENT DOCUMENTS

| | | | |
|---|---|---|---|
| 5,854,204 | A | 12/1998 | Findeis et al. |
| 5,858,979 | A | 1/1999 | Kakkar et al. |
| 5,872,210 | A | 2/1999 | Medabalimi |
| 5,932,550 | A | 8/1999 | Kato et al. |
| 6,184,210 | B1 | 2/2001 | Keanna et al. |
| 6,242,416 | B1 | 6/2001 | Gilchrest et al. |
| 6,258,932 | B1 | 7/2001 | Vahlne |
| 2002/0091086 | A1 | 7/2002 | Vahlne |

FOREIGN PATENT DOCUMENTS

| | | |
|---|---|---|
| FR | 2 668 488 A1 | 4/1992 |
| WO | WO 90/04390 | 5/1990 |
| WO | WO 92/20795 | 11/1992 |
| WO | WO 96/27386 | 9/1996 |
| WO | WO 96/28162 | 9/1996 |
| WO | WO 96/35714 | 11/1996 |
| WO | WO 98/09985 | 3/1998 |
| WO | WO 98/35062 | 8/1998 |
| WO | WO 99/09056 | 2/1999 |
| WO | WO 99/09985 | 3/1999 |
| WO | WO 00/09158 | 2/2000 |
| WO | WO 01/10456 | 2/2001 |
| WO | WO 01/10457 | 2/2001 |

OTHER PUBLICATIONS

Erickson et al., "Design, activity, and 2.8 A crystal structure of a C2 symmetric inhibior complexed to HIV–1 protease," Science, 249(4968):527–533 (1990).

Gamble et al., "Structure of the carboxyl–terminal dimerization domain of the HIV–1 capsid protein," Science, 278:849–853 (1997).

Grannelli–Piperno et al., "Efficient Interaction of HIV–1 with Purified Dendritic Cells via multiple chemokine Coreceptors," J Exp Med, 184:2433–2438 (1996).

Hall et al., "Substituted 4–hydroxyproline di–and tri–peptides as cytoxic agents," Amino Acids, 16(1):79–89 (1999).

Henderson et al., "Gag proteins of the highly replicative MN strain of human immunodeficiency virus type 1: postranslational modifications, proteolytic processing, and complete amino acid sequences," Journal of Virology, 66(4):1856–1865 (1992).

Hwang et al., "Identification of the envelope V3 loop as the primary determinant of cell tropism in HIV–1," Science, 253:71–74 (1991).

Kowalski et al., "Functional regions of the envelope glycoprotein of human immunodeficiency virus type I," Science, 237:1351–1355 (1987).

Lassila et al., "A Role for Lys–His–Gly–NH2 in Avian and Murine B Cell Development," Cell. Immun., 122:319–328, (1989).

Louis et al., "Hydrophilic peptides derived from the transframe region of GaPol inhibit the HIV–1 protease," Biochemistry, 37(8):2105–2110 (1998).

Martin, "Fast–acting slow viruses," Nature, 345:572–573 (1990).

Memar O. et al., "Antiviral Agents in Dermatology; Current Status and Future Prospects," Internation Journal of Dermatology, 34(9):597–606 (1995).

Miller et al., "Antiviral activity of carbobenzoxy Di–and Tripeptides on measles virus," Applied Microbiology, 16(10):1489–1496 (1968).

Niedrig et al., "Inhibition of Infectious human immunodeficiency virus type 1 particles formation by Gag protein derived peptides," Journal of General Virology, 75:1469–1474 (1994).

Palker et al., "Type–specific neutralization of the human immunodeficiency virus with antibodies to env–encoded synthetic peptides," Proc. Natl. Acad. Sci. USA, 85(6):1932–1936 (1988).

Richards, "Inhibition of the aspartic proteinase for HIV–2," FEBS Letters, 253(1,2):214–216 (1989).

Sheha et al., "Synthesis of di–and tripeptide analogues containing α–ketoamide as a new core structure for inhibition of HIV–1 protease," Eur. J. Med. Chem., 35(10):887–894 (2000).

Sigma, Peptide and Amino Acid Catalog, p. 27 and p. 70, Copyright 1995–96.

Su et al., "The nontoxic tripeptide glycyl–prolyl–glycine amide inhibits the replication of human immunodeficiency virus type 1," Journal of Human Virology, 4(1):1–7 (2001).

Su et al., "The tripeptide glycl–prolyl–glycine amide does not affect the early steps of the human immunodeficiency virus type 1 replication," Journal of Human Virology, 4(1):8–15 (2001).

Vahlne, "Protein Polymerization Inhibitors and Methods of Use," U.S. patent application Ser. No. 10/072,783, filed Feb. 8, 2002.

Van Der Spoel et al., "Pentamer Peptide Amide, ALG-PGNH2, which Inhibits Viral Infectivity and Methods of Use Thereof," U.S. patent application Ser. No. 10/217,933, filed Aug. 12, 2002.

Goobar–Larsson et al., "Molecules that Block Viral Infectivity and Methods of Use Thereof," U.S. patent application Ser. No. 10/217,933, filed Sep. 3, 2002.

Bachem Catalog, Bachem Bioscience Inc. 1993, pp. 28, 29, 34, 145, 267 ,332 ,333 ,457 ,535 ,536 ,541 , 546 and 553.

\* cited by examiner

```
hIV-1  SPTS-ILDIKQGKEPFRDYVDRFYKTLRAEQA---SQEVKNWMTETLLVQNANPDCKTILKALG-PAATLE-EMMTAC--QGVGGPGHK--ARVL//(SEQ. ID NO. 1)
HIV-2  NPTN-ILDIKQGKEPFQSYVDRFYKSLRAEQT---DPAVKNWMTQTLLIQNANPDCKLVLKGLG--MNPTLEEMLTAC--QGVGGPGQK--ARLM//(SEQ. ID NO2)
SIV    NPVN-ILDIKQGKEPFQSYVDRFYKSLRAEQA---DPAVKNWMTQTLLIQNANP DCKLVLKGLG--MNPTLEEMLTAC--QGVGGPGQK--ARLM//(SEQ. ID NO.3)
HTLV-1 DPS--WASILQGLEEPYHAFVERLNIALDNGLP---EGTPKDPILRSLAYSNANKECQKLLQARG--HTNSPLGDMLR AC--Q-TWTPKDK--TKVL--//(SEQ. ID NO. 4)
MPMV   DPGASLTGVKQGPDEPFADFVHRLITTAGRIFG--SAEAGVDYVKQLAYENANPACCQAAIRPYR--KKTDLTGYI LC--SDIGPSYQQGLAMA--//(SEQ ID NO.5)
MMTV   ---LAGLKQGNEESYETHSRLEEAVYRMMP--RGEGSDIL IKQLAWENAN SLCQDLIRPIR--KTGTIQDYI RAC--LDASPAV VQGMAY--//(SEQ. ID NO. 6)
MMLV   TN LAKVKGITQGPNESP SAFLERLKEAYRRYTPYDPEDPGQETNVSMSFIWQSA-PDIGRKLERLEDLRNKTL-GDLVREA--ERIFNKRE------//(SEQ. ID NO.7)
RSV    EPTDPWADIMQQPSESFVDFANRLIKA VEGSDL---P PSARAPVIIDCFRQKSQPDIQQLIRAAP--SILTTPGEIIKY VLDRQKTAPLTDQGIAAAM//(SEQ ID NO. 8)
              MHR
```

*FIG. 1*

SEQUENCE LISTING

```
<160> NUMBER OF SEQ ID NOS: 8

<210> SEQ ID NO 1
<211> LENGTH: 86
<212> TYPE: PRT
<213> ORGANISM: Artificial Sequence
<220> FEATURE:
<223> OTHER INFORMATION: Artificial Peptide

<400> SEQUENCE: 1

Ser Pro Thr Ser Ile Leu Asp Ile Lys Gln Gly Pro Lys Glu Pro Phe
 1               5                  10                  15
Arg Asp Tyr Val Asp Arg Phe Tyr Lys Thr Leu Arg Ala Glu Gln Ala
                20                  25                  30
Ser Gln Glu Val Lys Asn Trp Met Thr Glu Thr Leu Leu Val Gln Asn
            35                  40                  45
Ala Asn Pro Asp Cys Lys Thr Ile Leu Lys Ala Leu Gly Pro Ala Ala
        50                  55                  60
Thr Leu Glu Glu Met Met Thr Ala Cys Gln Gly Val Gly Gly Pro Gly
65                  70                  75                  80
His Lys Ala Arg Val Leu
```

<210> SEQ ID NO 2
<211> LENGTH: 86
<212> TYPE: PRT
<213> ORGANISM: Artificial Sequence
<220> FEATURE:
<223> OTHER INFORMATION: Artificial Peptide

<400> SEQUENCE: 2

```
Asn Pro Thr Asn Ile Leu Asp Ile Lys Gln Gly Pro Lys Glu Pro Phe
 1               5                  10                  15
Gln Ser Tyr Val Asp Arg Phe Tyr Lys Ser Leu Arg Ala Glu Gln Thr
            20                  25                  30
Asp Pro Ala Val Lys Asn Trp Met Thr Gln Thr Leu Leu Ile Gln Asn
        35                  40                  45
Ala Asn Pro Asp Cys Lys Leu Val Leu Lys Gly Leu Gly Met Asn Pro
    50                  55                  60
Thr Leu Glu Glu Met Leu Thr Ala Cys Gln Gly Val Gly Gly Pro Gly
65                  70                  75                  80
Gln Lys Ala Arg Leu Met
                85
```

<210> SEQ ID NO 3
<211> LENGTH: 86
<212> TYPE: PRT
<213> ORGANISM: Artificial Sequence
<220> FEATURE:
<223> OTHER INFORMATION: Artificial Peptide

<400> SEQUENCE: 3

```
Asn Pro Val Asn Ile Leu Asp Ile Lys Gln Gly Pro Lys Glu Pro Phe
 1               5                  10                  15
Gln Ser Tyr Val Asp Arg Phe Tyr Lys Ser Leu Arg Ala Glu Gln Ala
            20                  25                  30
Asp Pro Ala Val Lys Asn Trp Met Thr Gln Thr Pro Leu Ile Gln Asn
        35                  40                  45
Ala Asn Pro Asp Cys Lys Leu Val Leu Lys Gly Leu Gly Met Asn Pro
    50                  55                  60
Thr Leu Glu Glu Met Leu Thr Ala Cys Gln Gly Val Gly Gly Pro Gly
65                  70                  75                  80
Gln Lys Ala Arg Leu Met
                85
```

<210> SEQ ID NO 4
<211> LENGTH: 85
<212> TYPE: PRT
<213> ORGANISM: Artificial Sequence
<220> FEATURE:
<223> OTHER INFORMATION: Artificial Peptide

<400> SEQUENCE: 4

```
Asp Pro Ser Trp Ala Ser Ile Leu Gln Gly Leu Glu Glu Pro Tyr His
 1               5                  10                  15
Ala Phe Val Glu Arg Leu Asn Ile Ala Leu Asp Asn Gly Leu Pro Glu
            20                  25                  30
Gly Thr Pro Lys Asp Pro Ile Leu Arg Ser Leu Ala Tyr Ser Asn Ala
        35                  40                  45
Asn Lys Glu Cys Gln Lys Leu Leu Gln Ala Arg Gly His Thr Asn Ser
    50                  55                  60
Pro Leu Gly Asp Met Leu Arg Ala Cys Gln Thr Trp Thr Pro Lys Asp
65                  70                  75                  80
Lys Thr Lys Val Leu
                85
```

<210> SEQ ID NO 5
<211> LENGTH: 87
<212> TYPE: PRT
<213> ORGANISM: Artificial Sequence
<220> FEATURE:
<223> OTHER INFORMATION: Artificial Peptide

```
<400> SEQUENCE: 5

Asp Pro Gly Ala Ser Leu Thr Gly Val Lys Gln Gly Pro Asp Glu Pro
 1               5                  10                  15
Phe Ala Asp Phe Val His Arg Leu Ile Thr Thr Ala Gly Arg Ile Phe
                20                  25                  30
Gly Ser Ala Glu Ala Gly Val Asp Tyr Val Lys Gln Leu Ala Tyr Glu
            35                  40                  45
Asn Ala Asn Pro Ala Cys Gln Ala Ala Ile Arg Pro Tyr Arg Lys Lys
        50                  55                  60
Thr Asp Leu Thr Gly Tyr Ile Leu Cys Ser Asp Ile Gly Pro Ser Tyr
 65                 70                  75                  80
Gln Gln Gly Leu Ala Met Ala
                85

<210> SEQ ID NO 6
<211> LENGTH: 82
<212> TYPE: PRT
<213> ORGANISM: Artificial Sequence
<220> FEATURE:
<223> OTHER INFORMATION: Artificial Peptide

<400> SEQUENCE: 6

Leu Ala Gly Leu Lys Gln Gly Asn Glu Glu Ser Tyr Glu Thr Phe Ile
 1               5                  10                  15
Ser Arg Leu Glu Glu Ala Val Tyr Arg Met Met Pro Arg Gly Glu Gly
                20                  25                  30
Ser Asp Ile Leu Ile Lys Gln Leu Ala Trp Glu Asn Ala Asn Ser Leu
            35                  40                  45
Cys Gln Asp Leu Ile Arg Pro Ile Arg Lys Thr Gly Thr Ile Gln Asp
        50                  55                  60
Tyr Ile Arg Ala Cys Leu Asp Ala Ser Pro Ala Val Val Gln Gly Met
 65                 70                  75                  80
Ala Tyr

<210> SEQ ID NO 7
<211> LENGTH: 87
<212> TYPE: PRT
<213> ORGANISM: Artificial Sequence
<220> FEATURE:
<223> OTHER INFORMATION: Artificial Peptide

<400> SEQUENCE: 7

Thr Asn Leu Ala Lys Val Lys Gly Ile Thr Gln Gly Pro Asn Glu Ser
 1               5                  10                  15
Pro Ser Ala Phe Leu Glu Arg Leu Lys Glu Ala Tyr Arg Arg Tyr Thr
                20                  25                  30
Pro Tyr Asp Pro Glu Asp Pro Gly Gln Glu Thr Asn Val Ser Met Ser
            35                  40                  45
Phe Ile Trp Gln Ser Ala Pro Asp Ile Gly Arg Lys Leu Glu Arg Leu
        50                  55                  60
Glu Asp Leu Arg Asn Lys Thr Leu Gly Asp Leu Val Arg Glu Ala Glu
 65                 70                  75                  80
Arg Ile Phe Asn Lys Arg Glu
                85

<210> SEQ ID NO 8
<211> LENGTH: 93
<212> TYPE: PRT
<213> ORGANISM: Artificial Sequence
<220> FEATURE:
<223> OTHER INFORMATION: Artificial Peptide

<400> SEQUENCE: 8

Glu Pro Thr Asp Pro Trp Ala Asp Ile Met Gln Gly Pro Ser Glu Ser
 1               5                  10                  15
Phe Val Asp Phe Ala Asn Arg Leu Ile Lys Ala Val Glu Gly Ser Asp
                20                  25                  30
Leu Pro Pro Ser Ala Arg Ala Pro Val Ile Ile Asp Cys Phe Arg Gln
            35                  40                  45
```

```
                                -continued

Lys Ser Gln Pro Asp Ile Gln Gln Leu Ile Arg Ala Ala Pro Ser Thr
    50                  55                  60
Leu Thr Thr Pro Gly Glu Ile Ile Lys Tyr Val Leu Asp Arg Gln Lys
65              70                  75                  80
Thr Ala Pro Leu Thr Asp Gln Gly Ile Ala Ala Ala Met
                85                  90
```

TRIPEPTIDE AMIDES THAT BLOCK VIRAL INFECTIVITY AND METHODS OF USE THEREOF

FIELD OF THE INVENTION

The present invention relates to the discovery that certain tripeptide amides, which correspond to viral capsid sequences, can be used to inhibit viral infection, including human immunodeficiency virus (HIV) infection. More specifically, medicaments comprising these tripeptide amides and methods of using said compounds for the prevention and treatment of viral infection, such as HIV infection, are provided.

BACKGROUND OF THE INVENTION

All viruses are composed of a protein shell surrounding a nucleic acid containing core. The protein shell directly surrounding the viral nucleic acid is called a capsid, whereas, the complete protein-nucleic acid complex having both the capsid and the nucleic acid is called a nucleocapsid. Arenaviruses, rotaviruses, orbiviruses, retroviruses (including lentiviruses), papillomaviruses, adenoviruses, herpesviruses, paramyxovirus, myxovirus, and hepadnaviruses all exhibit these general structural features. (*Virology*, Fields ed., third edition, Lippencott-Raven publishers, pp 1513, 1645,1778, 2047, 2113, 2221, and 2717 (1996)).

The capsid is composed of many subunits (capsomeres) and capsomeres are formed from several homo- or hetero-polymers of protein. The noncovalent bonds between capsomeres in a viral assembly are of the same sort that stabilize a folded protein domain. The interface between two subunits can look very much like a single domain, with amino acid side chains tightly packed against one another. A common feature to most of the virus structures analyzed is the way in which a polypeptide chain from one capsomere can extend under or over domains of neighboring capsomeres. These extended polypeptide arms intertwine with other polypeptide arms and help to stabilize the capsid by initiating hydrophobic interactions, hydrogen bonding, and salt bridges. Contacts between individual capsomeres, and for some viruses also contacts with core proteins, determine the overall capsid structure and if a number of identical capsomeres are involved, repeated contacts occur and the resulting structure is symmnetrical. (Id. at 62).

Some simple viruses form spontaneously from their dissociated components while others require enzyme-catalyzed modifications of the capsomeres to trigger assembly. Viral self assembly is driven by the stability of the interactions between protein subunits under conditions that favor association. More complex viruses are often constructed from subassemblies that have undergone self assembly processes. (Id. at pp 62, 70, 1646 and 1888). Although the capsids of many viruses differ in protein composition, a general viral structural design has evolved characterized by polymerized capsomeres that, in turn, are composed of several homo- or hetero-polymers of protein.

HIV is the name given to a lentivirus that infects humans and that causes acquired immuno-deficiency syndrome (AIDS). The lentivirus isolates from humans are grouped into one of two types (HIV-1 and HIV-2) on the basis of serologic properties and sequence analysis of molecularly cloned viral genomes. Genetically distinct lentiviruses have been obtained from several non-human primate species including African green monkeys, sooty magabeys, mandrills, chimpanzees, and sykes. Collectively, the lentivirus isolates from non-human primates are called SIV. Sequence analysis reveals that the genomes of some SIV strains and HIV-1 and HIV-2 strains exhibit a high degree of homology. Further, electron microscopy reveals that the ultrastructure of HIV and SIV are similar in that both have virions about 110 nm in diameter with a cone-shaped nucleocapsid surrounded by a lipid bilayer membrane that contains envelope glycoprotein spikes. (Id. at pp.1882–1883).

HIV is a complex retrovirus containing at least seven genes. The viral structural genes, designated gag, pol, and env, respectively code for the viral core proteins, reverse transcriptase, and the viral glycoproteins of the viral envelope. The remaining HIV genes are accessory genes involved in viral replication. The gag and env genes encode polyproteins, i.e., the proteins synthesized from each of these genes are post-translationally cleaved into several smaller proteins.

Although the overall shape of HIV and SIV virions is spherical, the nucleocapsid is asymmetrical having a long dimension of about 100 nm, a wide free end about 40–60 nm, and a narrow end about 20 nm in width. The nucleocapsid within each mature virion is composed of two molecules of the viral single-stranded RNA genome encapsulated by proteins proteolytically processed from the Gag precursor polypeptide. Cleavage of the gag gene polyprotein Pr55$^{gag}$ by a viral coded protease (PR) produces mature capsid proteins. These gag gene products are the matrix protein (p17), that is thought to be located between the nucleocapsid and the virion envelope; the major capsid protein (p24), that forms the capsid shell; and the nucleocapsid protein (p9), that binds to the viral RNA genome. This proteolytic processing in infected cells is linked to virion morphogenesis. (Id. at pp 1886–1887).

The major capsid protein p24 (also called CA) contains about 240 amino acids and exhibits a molecular weight of 24–27 kD. The protein p24 self-associates to form dimers and oligomeric complexes as large as dodecamers. Genetic studies with mutations in the HIV-1 gag polyprotein have identified several functional domains in the p24 protein including the C terminal half of the molecule and a major homology region (MHR) spanning 20 amino acids that is conserved in the p24 proteins of diverse retroviruses. These mutations appear to affect precursor nucleocapsid assembly. (Id. at pp 1888–1889).

Since the discovery of HIV-1 as the etiologic agent of AIDS, significant progress has been made in understanding the mechanisms by which the virus causes disease. While many diagnostic tests have been developed, progress in HIV vaccine therapy has been slow largely due to the heterogeneous nature of the virus and the lack of suitable animal models. (See, e.g., Martin, *Nature*, 345:572–573 (1990)).

A variety of pharmaceutical agents have been used in attempts to treat AIDS. Many, if not all, of these drugs, however, create serious side effects that greatly limit their usefulness as therapeutic agents. HIV reverse transcriptase is one drug target because of its crucial role in viral replication. Several nucleoside derivatives have been found to inhibit HIV reverse transcriptase including azidothymidine (AZT, zidovidine®). AZT causes serious side effects such that many patients cannot tolerate its administration. Other nucleoside analogs that inhibit HIV reverse transcriptase have been found to cause greater side effects than AZT. Another drug target is the HIV protease (PR) crucial to virus development. PR is an aspartic protease and can be inhibited by synthetic compounds. (Richards, *FEBS Lett.*, 253:214–216 (1989)). Protease inhibitors inhibit the growth of HIV more effectively than reverse transcriptase inhibitors but prolonged therapy has been associated with metabolic diseases such as lipodystrophy, hyperlipidemia, and insulin resistance.

Additionally, HIV quickly develops resistance to nucleoside/nucleotide analogue reverse transcriptase inhibitors and protease inhibitors. This resistance can also spread between patients. Studies have shown, for example, that one tenth of the individuals recently infected by HIV already have developed resistance to AZT, probably because they were infected by a person that at the time of transmission carried a virus that was resistant to AZT.

It would be useful in the treatment and prevention of viral infections, including HIV and SIV, to have specific and selective therapeutic agents that cause few, if any, side effects.

SUMMARY OF THE INVENTION

The present invention is related to tripeptide amides that inhibit viral infectivity. An intact capsid structure is of vital importance for the infectivity of a virion. A way to disrupt assembly of capsid protein macromolecules, that for their infectivity are dependent on di-, tri-, tetra-, or poly-merization, is to construct small molecules that affect such protein-protein interactions. It was discovered that tripeptides with their carboxyl terminus hydroxyl group replaced with an amide group have such an inhibiting effect on capsid-protein interactions. Thus, aspects of the present invention relate to tripeptide amides that affect viral capsid assembly.

In desirable embodiments, the tripeptide amides bind to a protein that is involved in capsomere organization and capsid assembly of HIV-1, HIV-2, and SIV and thereby inhibit and/or prevent proper capsid assembly and, thus, viral infection. The tripeptide amides Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$ are the preferred species. These tripeptide amides and peptidomimetics resembling their structure (collectively referred to as "peptide agents") are used in a monomeric or multimeric form. The tripeptide amides are suitable for therapeutic and prophylactic application in mammals, including man, suffering from viral infection.

In one embodiment, a composition for inhibiting viral replication in host cells infected with a virus has an effective amount of a peptide in amide form selected from the group of Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. In some embodiments, the compositions described above are joined to a support and in other embodiments, the compositions described above are incorporated into a pharmaceutical having a pharmaceutically acceptable carrier. For example, the peptide in amide form can have the formula Ser Ile-Leu-$NH_2$ and can be joined to a support.

Methods of inhibiting viral replication in a host cell are also embodiments of the present invention. One approach, for example, involves administering to a cell an effective amount of a peptide in amide form selected from the group consisting of Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. The method described above can be supplemented with an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. The tripeptide amide used in the method above can be joined to a support or can be administered in a pharmaceutical comprising a pharmaceutically acceptable carrier.

In another embodiment, a composition for inhibiting HIV replication in host cells includes an effective amount of a peptide in amide form selected from the group consisting of Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. In some embodiments, these tripeptide amides are joined to a support and in other embodiments, these peptides are incorporated into a pharmaceutical comprising a pharmaceutically acceptable carrier.

In another method, an approach to inhibit HIV replication in host cells is provided, which involves administering to said cells an effective amount of a peptide in amide form selected from the group consisting of peptides of the formula Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. This method can also be supplemented by an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the tripeptide amide used in this method can be joined to a support or can be administered in a pharmaceutical comprising a pharmaceutically acceptable carrier.

In another method, an approach for interrupting viral capsid assembly is provided. This approach involves contacting a cell with an effective amount of a peptide in amide form selected from the group consisting of peptides of the formula Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. The tripeptide amide can be joined to a support or incorporated in a pharmaceutical.

In still another method, an approach for interrupting HIV capsid assembly is provided. This approach also involves contacting a cell with an effective amount of a peptide in amide form selected from the group consisting of peptides of the formula Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. The tripeptide amide of this method can be joined to a support or incorporated in a pharmaceutical.

Methods of identification of peptide agents that inhibit viral replication, specifically HIV replication are also provided. By one method, for example, a peptide agent for incorporation into an anti-viral pharmaceutical is identified by contacting a plurality of cells infected with a virus with an effective amount of a peptide agent, analyzing the virus for incomplete capsid formation, and selecting the peptide agent that induces incomplete capsid formation. This method can involve an analysis of capsid formation that employs microscopy and the virus can be selected from the group consisting of HIV-1, HIV-2, and SIV. Further, the peptide agent identified can be selected from the group consisting of a tripeptide amide and a peptidomimetic resembling a tripeptide amide. For example, the peptide agent above can be selected from the group consisting of Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. In a preferred embodiment, the peptide agent used in the method above has an amino acid sequence that corresponds to an amino acid sequence of p24.

In another embodiment, a method of identifying a peptide agent that binds to a viral protein is provided. Some aspects of this method involve providing a viral protein, contacting the viral protein with an effective amount of a peptide agent, and detecting the formation of a complex comprising the viral protein and the peptide agent. Some methods use a viral protein that is from a virus selected from the group consisting of HIV-1, HIV-2, and SIV. Further, in some embodiments, the peptide agent is selected from the group consisting of a tripeptide amide and a peptidomimetic resembling a tripeptide amide. Desirably, the method above employs a peptide agent selected from the group consisting of Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. Additionally, a method of making a pharmaceutical is provided in which the peptide agent identified by the methods above are incorporated in a pharmaceutical.

Another approach to making a pharmaceutical involves administering to a cell an effective amount of a peptide in amide form, described above, detecting an inhibition of viral replication in the cell, and incorporating the peptide that causes inhibition of viral replication into the pharmaceutical. This method can involve the use of a tripeptide amide selected from the group consisting of Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. Further, this method can be supplemented with administration of an antiviral compound selected from the group consisting of nucleoside analogue reverse transcriptase inhibitors, nucleotide analogue reverse transcriptase inhibitors, non-nucleoside reverse transcriptase inhibitors, and protease inhibitors into the pharmaceutical. Additionally, the method above can be supplemented by incorporating a carrier into the pharmaceutical.

In another embodiment, a composition for inhibiting viral replication in host cells infected with a virus includes an effective amount of a peptide of the formula $X_1X_2X_3$—R, wherein $X_1$, $X_2$, and $X_3$ are any amino acid, wherein R is a modulation group attached to the carboxy-terminus of said peptide and R comprises an amide group or other moiety having similar charge and steric bulk and wherein said composition inhibits viral replication by interrupting viral capsid assembly. This composition can be a peptide selected from the group consisting of peptides having the formula Ser-Ile-Leu-R, Ile-Leu-Asp-R, Gly-Pro-Lys-R, Pro-Lys-Glu-R, Lys-Glu-Pro-R, Glu-Pro-Phe-R, Arg-Asp-Tyr-R, Asp-Tyr-Val-R, Tyr-Lys-Thr-R, Arg-Ala-Glu-R, Ala-Glu-Gln-R, Glu-Gln-Ala-R, Val-Lys-Asn-R, Thr-Glu-Thr-R, Leu-Leu-Val-R, Val-Gln-Asn-R, Gln-Asn-Ala,-R, Asn-Ala-Asn-R, Asn-Pro-Asp-R, Pro-Asp-Cys-R, Cys-Lys-Thr-R, Thr-Ile-Leu-R, Ala-Leu-Gly-R, Pro-Gly-Ala-R, Thr-Leu-Glu-R, Thr-Ala-Cys-R, Ala-Cys-Gln-R, Gln-Gly-Val-R, Pro-Gly-His-R, and Arg-Val-Leu-R. Desirably, $X_3$ is glycine in these embodiments.

BRIEF DESCRIPTION OF THE DRAWINGS

FIG. 1 illustrates an alignment of the protein sequence corresponding to the carboxyl terminus of the HIV-1 p24 protein (residues 146–231) and protein sequences of HIV-2, SIV, Rous Sarcoma virus (RSV), human T cell lymphotrophic virus-type 1 (HTLV-1), mouse mammary tumor virus (MMTV), Mason-Pfizer monkey virus (MPMV), and Moloney murine leukemia virus (MMLV). The bar represents the major homology region(MHR).

DETAILED DESCRIPTION OF THE PREFERRED EMBODIMENT

It has been discovered that tripeptide amides with sequences that correspond to viral capsid proteins prevent and/or inhibit viral infection by interrupting proper nucleocapsid formation. Such peptides are useful in the treatment of viral disease, particularly in HIV/AIDS afflicted subjects, and as preventive agents for patients at-risk of viral infection, particularly HIV infection, and for use with medical devices where the risk of exposure to virus is significant.

The disclosure below demonstrates that tripeptides in amide form of a sequence that corresponds to viral proteins, such as Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-le-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$ inhibit the replication of viruses, such as HIV-1, HIV-2, and SIV. Evidence of the inhibition of viral replication was found in viral infectivity assays that monitor the amount of capsid protein or reverse transcriptase activity present in culture supernatant.

Electron microscopic images of HIV particles treated with tripeptide amides also reveal that this novel class of antiviral agent interrupts proper capsid assembly in a manner distinct from protease inhibitors. Further, in vitro binding assays demonstrate that the tripeptide amides bind to the major capsid protein (p24) of HIV-1. Because the sequences of several viral capsid proteins are known, such as for members of arenavirus, rotavirus, orbivirus, retrovirus, papillomavirus, adenovirus, herpesvirus, paramyxovirus, myxovirus, and hepadnavirus families, several tripeptide amides that correspond to these sequences can be selected and rapidly screened to identify which ones effectively inhibit and/or prevent viral infection by using the viral infectivity assays described herein, or modifications of these assays as would be apparent to those of skill in the art given the present disclosure.

Several approaches to making biotechnological tools and pharmaceutical compositions comprising tripeptide amides and peptidomimetics that resemble tripeptide amides (collectively referred to as "peptide agents") that correspond to sequences of viral capsid proteins are given below. Preferred peptide agents are tripeptides with an amide group at their carboxy termini, and include the following: Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. In some embodiments, the peptide agents are provided in monomeric form; in others, the peptide agents are provided in multimeric form or in multimerized form. Support-bound peptide agents are also used in several embodiments.

Pharmaceutical compositions comprising peptide agents are administered as therapeutics or prophylactics or both for the treatment and/or prevention of viral disease, particularly, HIV infection. In some embodiments, the pharmaceutical compositions comprising peptide agents are administered in combination with other antiviral treatments including nucleoside analogue reverse transcriptase inhibitors, nucleotide analogue reverse transcriptase inhibitors, non-nucleoside reverse transcriptase inhibitors, and protease inhibitors. These small peptides are resistant to acid hydrolysis. A significant amount of tripeptide amides is effectively delivered to blood, plasma, and organ tissue when administered to test subjects. The administration of large doses of small peptides to test subjects is relatively nontoxic. (See U.S. Pat. No. 6,258,932B1, which is herein expressly incorporated by reference in its entirety).

Additionally, several methods of identifying a peptide agent that inhibits or prevents viral replication or interrupts viral capsid assembly or both are provided. By one approach, an effective amount of a peptide agent is contacted with cells infected with a virus and the cells are analyzed for viral replication or the presence of viral products. Accordingly, a capsid protein (e.g., p24) is contacted with a peptide agent, for example a peptide in amide form, as described above, and a complex comprising the capsid protein (e.g., p24) bound with the peptide agent is identified.

The amide form of the tripeptides listed in TABLE 1 were first tested. Many of these tripeptides were selected and synthesized because they either fully or partially correspond to sequences in HIV and/or SIV viral proteins. The tripeptide amides of TABLE 1 were synthesized according to the method disclosed in EXAMPLE 1 below, but could of course be synthesized by any method known in the art.

TABLE 1

| Amino Acid Sequence of Peptides Tested | |
|---|---|
| Ser-Ile-Leu-NH$_2$ | Thr-Glu-Thr-NH$_2$ |
| Ile-Leu-Asp-NH$_2$ | Leu-Leu-Val-NH$_2$ |
| Gly-Pro-Lys-NH$_2$ | Val-Gln-Asn-NH$_2$ |
| Pro-Lys-Glu-NH$_2$ | Gln-Asn-Ala-NH$_2$ |
| Lys-Glu-Pro-NH$_2$ | Asn-Ala-Asn-NH$_2$ |
| Glu-Pro-Phe-NH$_2$ | Asn-Pro-Asp-NH$_2$ |
| Arg-Asp-Tyr-NH$_2$ | Pro-Asp-Cys-NH$_2$ |
| Asp-Tyr-Val-NH$_2$ | Cys-Lys-Thr-NH$_2$ |
| Tyr-Lys-Thr-NH$_2$ | Thr-Ile-Leu-NH$_2$ |
| Arg-Ala-Glu-NH$_2$ | Ala-Glu-Gln-NH$_2$ |
| Pro-Gly-Ala-NH$_2$ | Arg-Val-Leu-NH$_2$ |
| Glu-Gln-Ala-NH$_2$ | Thr-Leu-Glu-NH$_2$ |
| Val-Lys-Asn-NH$_2$ | Thr-Ala-Cys-NH$_2$ |
| Ala-Cys-Gln-NH$_2$ | Gln-Gly-Val-NH$_2$ |
| Pro-Gly-His-NH$_2$ | |
| Abbreviations Used: | |
| Leu-Leucine | Lys-Lysine |
| Gln-Glutamine | Ala-Alanine |
| His-Histidine | Ileu-Isoleucine |
| Cys-Cysteine | Gly-Glycine |
| Pro-Proline | Arg-Arginine |
| Val-Valine | Thr-Threonine |
| Ser-Serine | Asn-Asparagine |
| Phe-Phenylalanine | Asp-Aspartate |
| Tyr-Tyrosine | Glu-Glutamate |

EXAMPLE 1

In this example, the approaches used to obtain the tripeptide amides listed above are disclosed. The tripeptide amides were chemically synthesized with an automated peptide synthesizer (Syro, Multisyntech, Tubingen, Germany). The synthesis was run using 9-fluorenylmethoxycarbonyl (fmoc) protected amino acids (Milligen, Bedford, Mass.) according to standard protocols. All peptides were lyophilized and then dissolved at the appropriate concentration in phosphate-buffered saline (PBS). The peptides were analyzed by reverse phase high performance liquid chromatography (RP-HPLC) using a PepS-15 C18 column (Pharmacia, Uppsala, Sweden).

The modified peptides were created by substituting an amino group for the hydroxyl residue normally present at the terminal carboxyl group of a peptide. That is, instead of a terminal COOH, the peptides were synthesized to have $CO-NH_2$. For example, preferred tripeptide amides include Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. In the disclosure below, several assays that were used to identify tripeptide amides that inhibit HIV-1 infection are described.

Small Peptides Inhibit and/or Prevent HIV Replication and Infection

The tripeptide amides made according to EXAMPLE 1 were used in several HIV-1 infectivity assays to determine the ability of said tripeptide amides to inhibit HIV replication and/or infection. The efficiency of HIV-1 replication and status of HIV-1 infection was monitored by reverse transcriptase activity and the concentration of p24 protein in the cell supernatant. (See e.g., U.S. Pat. Nos. 5,627,035 and 6,258,932B1, herein expressly incorporated by reference in their entireties, which describe similar HIV infectivity assays and others that can be used to analyze the tripeptide amides described herein). EXAMPLE 2 describes an approach that was used to screen several tripeptide amides for their ability to inhibit HIV-1 infection.

EXAMPLE 2

In this example, the methods that were used to analyze the ability of various tripeptide amides to inhibit HIV-1 replication are disclosed. Approximately $10^5$ of H9 cells were infected with HIV-1 SF-2 at 25 $TCID_{50}$ to test the inhibitory effect of the following synthesized tripeptides: Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. Accordingly, the H9 cells were resuspended with or without the different peptides (approximately 100 $\mu$m) in 1 ml of RPMI 1640 medium supplemented with 10% (v/v) heat-inactivated fetal bovine serum (FBS), penicillin (100 $\mu$/ml), and streptomycin (100 $\mu$/ml), all available through GIBCO, and Polybrene (2 $\mu$g/ml), available through Sigma. Thereafter, viruses were added at 25 $TCID_{50}$ in a volume of 20–30 $\mu$l. Cells were incubated with virus at 37° C. for 1 hr then pelleted at 170×g for 7 minutes. The cells were then washed three times in RPMI medium with or without peptides at room temperature and pelleted at 170×g for 7 minutes, as above. After the final wash, the cells were resuspended in RPMI culture medium containing the peptides in a 24-well plate (Costar corporation) and were kept at 37° C. in 5% $CO_2$ with humidity.

Culture supernatants were collected and analyzed when the medium was changed at 4, 7, 10, and 14 days post infection. To monitor the replication of virus, reverse transcriptase (RT) activity in the supernatants was assayed using a commercially available Lenti-RT activity kit. (Cavidi Tech, Uppsala, Sweden). The amount of RT was determined with the aid of a regression line of standards.

The presence of p24 in the supernatants was determined using a commercially available HIV p24 antigen detection kit (ELISA kit from Abbott Laboratories, North Chicago, U.S.A.). In some cases, serial dilutions of the supernatants were made so as to more accurately detect p24 concentration. As discussed in greater detail below, it was discovered that the tripeptide amides Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$ effectively inhibit HIV-1 infection.

As shown in TABLES 2 and 3, twenty nine (29) tripeptide amides from the C-terminal domain of HIV-1 p24 (from residues 146 to 231) demonstrated antiviral activity at 100 $\mu$M concentration as determined by p24 production and RT activity in the culture supernatants. Four (4) tripeptide amides with >80% inhibitory effect are shown in TABLE 2. Twenty five (25) tripeptides amides with 50–79% inhibitory effect are shown in TABLE 3. The section below describes approaches to design and analyze tripeptide amides for the ability to inhibit the replication and/or infection of other viruses.

TABLE 2

Tripeptide amides with more than 80% antiviral inhibitory activity as determined by p24 production and RT activity in the culture supernatants.

| Pro-Lys-Glu-$NH_2$ | Glu-Pro-Phe-$NH_2$ |
|---|---|
| Thr-Leu-Glu-$NH_2$ | Arg-Val-Leu-$NH_2$ |

TABLE 3

Tripeptide amides with more than 50–79% antiviral inhibitory activity as determined by p24 production and RT activity in the culture supernatants.

| Ser-Ile-Leu-$NH_2$ | Ile-Leu-Asp-$NH_2$ |
|---|---|
| Gly-Pro-Lys-$NH_2$ | Lys-Glu-Pro-$NH_2$ |
| Arg-Asp-Tyr-$NH_2$ | Asp-Tyr-Val-$NH_2$ |
| Tyr-Lys-Thr-$NH_2$ | Arg-Ala-Glu-$NH_2$ |
| Ala-Glu-Gln-$NH_2$ | Glu-Gln-Ala-$NH_2$ |
| Val-Lys-Asn-$NH_2$ | Thr-Glu-Thr-$NH_2$ |
| Leu-Leu-Val-$NH_2$ | Val-Gln-Asn-$NH_2$ |
| Gln-Asn-Ala-$NH_2$ | Asn-Ala-Asn-$NH_2$ |
| Pro-Asp-Cys-$NH_2$ | Cys-Lys-Thr-$NH_2$ |
| Pro-Gly-Ala-$NH_2$ | Thr-Ala-Cys-$NH_2$ |

TABLE 3-continued

Tripeptide amides with more than 50–79% antiviral inhibitory activity as determined by p24 production and RT activity in the culture supernatants.

| | |
|---|---|
| Gln-Gly-Val-NH$_2$ | Pro-Gly-His-NH$_2$ |
| Asn-Pro-Asp-NH$_2$ | Thr-Ile-Leu-NH$_2$ |
| Ala-Cys-Gln-NH$_2$ | |

Small Peptides Inhibit and/or Prevent Viral Replication and Infection

Several viral capsid proteins contain a 20 amino acid long homology region called the major homology region (MHR), that exists within the carboxyl-terminal domain of many onco- and lentiviruses. FIG. 1 shows the carboxyl-terminal domain of HIV-1 (residues 146–231) and compares this sequence to the capsid protein sequences of other viruses, some of which infect birds, mice, and monkeys. Notably, considerable homology in the sequences of these viral capsid proteins is found. Investigators have observed that the carboxyl-terminal domain is required for capsid dimerization and viral assembly in HIV-1. (Gamble et al., *Science* 278: 849 (1997), herein incorporated by reference in its entirety). While the tripeptide amides that exhibited antiviral activity in the assays described above fully or partially corresponded to regions of the carboxyl-terminal domain of HIV-1, HIV-2, or SfV, regions of the N-terminal domain of viruses are important for capsid assembly and the design and synthesis of tripeptide amides that either fully or partially correspond to amino acids of the N-terminal region of viral capsid proteins are desirable embodiments. The use of tripeptide amides that fully or partially correspond to amino acids within the MHR region and the carboxyl-terminal domain of viral capsid proteins, however, are preferred.

Tripeptide amides that inhibit capsid assembly of several other viruses can be made and screened using approaches similar to those described above. By designing and manufacturing tripeptide amides and/or peptidomimetics that resemble tripeptide amides and that correspond to regions of the sequences disclosed in FIG. 1, for example, new molecules that inhibit HIV, SIV, RSV, HTLV-1, MMTV, MPMV, and MMLV infection can be rapidly identified. To this end, the screening techniques discussed above or modifications of these assays, as would be apparent to one of skill in the art can also be used.

Further, many of the sequences of other viral capsid proteins are known, such as for members of the arenavirus, rotavirus, orbivirus, retrovirus, papillomavirus, adenovirus, herpesvirus, paramyxovirus, myxovirus, and hepadnavirus families.

Several tripeptide amides or peptidomimetics that resemble tripeptide amides and that fully or partially correspond to these sequences can be selected and rapidly screened to identify those that effectively inhibit and/or prevent viral infection by using the viral infectivity assays and/or electron microscopy techniques described herein, or modifications of these assays as would be apparent to those of skill in the art given the present disclosure.

For example, to test the ability of tripeptide amides to suppress the growth of mammalian DNA viruses, anti-viral screening against Herpes Simplex Type 1 (HSV-1) and Herpes Simplex Type 2 (HSV-2) can be performed in tissue culture using Human Foreskin Fibroblast cells. (See e.g., U.S. Pat. No. 6,248,782 to Elford, et al., expressly incorporated by reference in its entirety). In these infectivity assays, a semi-automated CPE-inhibition assay can be used employing HSV-1 E-377 strain and HSV-2 MS strain. Additionally, the ability of tripeptide amides to inhibit cytomegalo virus (CMV) can be determined using a semi-automated CPE inhibition assay and the AD169 strain and for varicellovirus (VZV), a plaque reduction assay using ELLEN strain. Tripeptide amides can also be screened against Epstein Barr Virus (EBV) in Raji cells (a Burkitt's lymphoma cell line containing 60 EBV genomes/cell) using an immunofluorescence assay with monoclonal antibodies directed against EBV components.

Toxicity can be determined by visual inspection of treated cells, generally stationary cells and a cell proliferation assay can be carried out by determining the presence of rapidly growing cells and either an EC$_{50}$ (concentration required to inhibit viral cytopathogenicity by 50%) or an IC$_{50}$ (concentration μg/ml) required to inhibit cell proliferation 50%) can be calculated. Also a Selective Index (S.I.) IC$_{50}$/EC$_{50}$ can be determined. As above, it is expected that a 100 μM concentration of tripeptide amide in these assays would be sufficient to significantly inhibit the replication and/or infectivity of HSV, CMV, VZV, and EBV.

Tripeptide amides that inhibit viral replication include the tripeptide amides Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NE$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. Peptidomimetics that resemble Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$ are also embodiments of the present invention.

It is preferred that the tripeptides possess a modulation group (e.g., an amide group) at their carboxy termini (CO—NH$_2$) rather than a carboxyl group (COOH). Tripeptides having other modulation groups at the carboxy terminus, can also be used but desirably, the attached modulation groups have the same charge and sterically behave the same as an amide group. (See U.S. Pat. No. 5,627,035 to Vahlne et al., for an assay to compare peptides having differing substituents at the carboxyl terminus, herein incorporated by reference in its entirety). In some embodiments, the addition of an acetyl or methyl group at either end of a small peptide is desirable so as to improve uptake of the small peptide or prevent exo-protease digestion or both. In the following section, several approaches are provided to make biotechnological tools and pharmaceutical compositions comprising tripeptide amides.

Biotechnological Tools and Pharmaceutical Compositions Comprising Tripeptide Amides Desirable biotechnological tools or components to prophylactic or therapeutic agents provide the tripeptide amides in such a form or in such a way that a sufficient affinity for inhibition of a virus, such as HIV-1, HIV-2, or SIV, is obtained. While a natural monomeric peptide agent (e.g., appearing as discrete units of the peptide agent each carrying only one binding epitope) is sufficient to bind a capsomere protein, such as p24, and/or interfere with capsid assembly and/or prevent viral infection, such as HIV-1, HIV-2, or SIV infection, synthetic ligands or multimeric ligands (e.g., appearing as multiple units of the peptide agent with several binding epitopes) may have far greater ability to bind a capsomere protein, such as p24, and/or interfere with capsid assembly and/or prevent viral infection, such as HIV-1, HIV-2, or SIV infection. It should be noted that the term "multimeric" refers to the presence of more than one unit of a ligand, for example several individual molecules of a tripeptide amide, as distinguished from the term "multimerized" that refers to the presence of more than one tripeptide amide joined as a single discrete unit in tandem.

A multimeric agent (synthetic or natural) that binds a capsomere protein, such as p24, and/or interferes with capsid assembly and/or inhibits viral infection, such as HIV-1, HIV-2, or SIV infection, may be obtained by coupling a tripeptide amide to a macromolecular support. The term "support" as used herein includes a carrier, a resin or any macromolecular structure used to attach, immobilize, or stabilize a peptide agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, artificial cells and others. The term "support" also includes carriers as that term is understood for the preparation of pharmaceuticals.

The macromolecular support can have a hydrophobic surface that interacts with a portion of the peptide agent by hydrophobic non-covalent interaction. The hydrophobic surface of the support can also be a polymer such as plastic or any other polymer in which hydrophobic groups have been linked such as polystyrene, polyethylene or polyvinyl. Alternatively, the peptide agent can be covalently bound to carriers including proteins and oligo/polysaccharides (e.g. cellulose, starch, glycogen, chitosane or aminated sepharose). In these later embodiments, a reactive group on the peptide agent, such as a hydroxy or an amino group, can be used to join to a reactive group on the carrier so as to create the covalent bond. The support can also have a charged surface that interacts with the peptide agent. Additionally, the support can have other reactive groups that can be chemically activated so as to attach a peptide agent. For example, cyanogen bromide activated matrices, epoxy activated matrices, thio and thiopropyl gels, nitrophenyl chloroformate and N-hydroxy succinimide chlorformate linkages, and oxirane acrylic supports are common in the art.

The support can also comprise an inorganic carrier such as silicon oxide material (e.g. silica gel, zeolite, diatomaceous earth or aminated glass) to which the peptide agent is covalently linked through a hydroxy, carboxy or amino group and a reactive group on the carrier. Furthermore, in some embodiments, a liposome or lipid bilayer (natural or synthetic) is contemplated as a support and peptide agents are attached to the membrane surface or are incorporated into the membrane by techniques in liposome engineering. By one approach, liposome multimeric supports comprise a peptide agent that is exposed on the surface of the bilayer and a second domain that anchors the peptide agent to the lipid bilayer. The anchor can be constructed of hydrophobic amino acid residues, resembling known transmembrane domains, or can comprise ceramides that are attached to the first domain by conventional techniques.

Supports or carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine, liposomes, and Chromosorb® (Johns-Manville Products, Denver Colo.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases,* 171:1042–1045 (1995)). For some embodiments, the administration of a "naked" carrier (i.e., lacking an attached peptide agent) that has the capacity to attach a peptide agent in the body of a subject is contemplated. By this approach, a "prodrug-type" therapy is envisioned in which the naked carrier is administered separately from the peptide agent and, once both are in the body of the subject, the carrier and the peptide agent are assembled into a multimeric complex.

The insertion of linkers, such as A linkers, of an appropriate length between the peptide agent and the support are also contemplated so as to encourage greater flexibility of the peptide agent and thereby overcome any steric hindrance that may be presented by the support. The determination of an appropriate length of linker that allows for optimal binding to a capsomere protein, such as p24, and/or interference with capsid assembly and/or inhibition of viral infection, such as HIV or SIV infection, can be determined by screening the peptide agents with varying linkers in the assays detailed in the present disclosure.

Another aspect of the invention includes a composite support comprising more than one type of peptide agent is also an embodiment. A "composite support" may be a carrier, a resin, or any macromolecular structure used to attach or immobilize two or more different peptide agents that bind to a capsomere protein, such as p24, and/or interfere with capsid assembly and/or inhibit viral infection, such as HIV or SIV infection. In some embodiments, a liposome or lipid bilayer (natural or synthetic) is contemplated for use in constructing a composite support and peptide agents are attached to the membrane surface or are incorporated into the membrane using techniques in liposome engineering.

The insertion of linkers, such as A linkers, of an appropriate length between the peptide agent and the support is also contemplated so as to encourage greater flexibility in the molecule and thereby overcome any steric hindrance that may occur. The determination of an appropriate length of linker that allows for optimal binding to a capsomere protein, such as p24, and/or interference with capsid assembly and/or inhibition of viral infection, such as HIV or SIV infection, can be determined by screening the ligands with varying linkers in the assays detailed in the present disclosure.

In other embodiments, the multimeric and composite supports discussed above can have attached multimerized ligands so as to create a "multimerized-multimeric support" and a "multimerized-composite support", respectively. A multimerized ligand can, for example, be obtained by coupling two or more peptide agents in tandem using conventional techniques in molecular biology. The multimerized form of the ligand can be advantageous for many applications because of the ability to obtain an agent with a better ability to bind to a capsomere protein, such as p24, and/or interfere with capsid assembly and/or inhibit viral infection, such as HIV or SIV infection. Further, the incorporation of linkers or spacers, such as flexible λ linkers, between the individual domains that make-up the multimerized agent is another embodiment. The insertion of λ linkers of an appropriate length between protein binding domains, for example, can encourage greater flexibility in the molecule and can overcome steric hindrance. Similarly, the insertion of linkers between the multimerized ligand and the support can encourage greater flexibility and limit steric hindrance presented by the support. The determination of an appropriate length of linker that allows for optimal binding to p24 and/or interference with capsid assembly and/or inhibition of HIV or SIV infection, can be determined by screening the ligands with varying linkers in the assays detailed in this disclosure.

In preferred embodiments, the various types of supports discussed above are created using the tripeptide amides Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NH_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$. The multimeric supports, composite supports, multimerized-multimeric supports, or multimerized-composite supports, collectively referred to as "support-bound agents", are also preferably constructed using the tripeptide amides Ser-Ile-Leu-$NH_2$, Ile-Leu-Asp-$NH_2$, Gly-Pro-Lys-$NH_2$, Pro-Lys-Glu-$NH_2$, Lys-Glu-Pro-$NH_2$, Glu-Pro-Phe-$NH_2$, Arg-Asp-Tyr-$NH_2$, Asp-Tyr-Val-$NH_2$, Tyr-Lys-Thr-$NH_2$, Arg-Ala-Glu-$NH_2$, Ala-Glu-Gln-$NH_2$, Glu-Gln-Ala-$NE_2$, Val-Lys-Asn-$NH_2$, Thr-Glu-Thr-$NH_2$, Leu-Leu-Val-$NH_2$, Val-Gln-Asn-$NH_2$, Gln-Asn-Ala,-$NH_2$, Asn-Ala-Asn-$NH_2$, Asn-Pro-Asp-$NH_2$, Pro-Asp-Cys-$NH_2$, Cys-Lys-Thr-$NH_2$, Thr-Ile-Leu-$NH_2$, Pro-Gly-Ala-$NH_2$, Thr-Leu-Glu-$NH_2$, Thr-Ala-Cys-$NH_2$, Ala-Cys-Gln-$NH_2$, Gln-Gly-Val-$NH_2$, Pro-Gly-His-$NH_2$, and Arg-Val-Leu-$NH_2$.

The monomeric and multimeric peptide agents described herein are suitable for use as a biotechnological tool to study the interaction of tripeptide amides with capsid proteins and also as medicaments for the treatment of subjects already infected with a virus, such as HIV or SIV, or as a preventive measure to avoid viral infections, such as HIV or SIV infection. Although anyone could be treated with the tripeptide amides as a prophylactic, the most suitable subjects are people at risk for viral infection. Such subjects include, but are not limited to, the elderly, the chronically ill, homosexuals, prostitutes, intravenous drug users, hemophiliacs, children, and those in the medical profession who have contact with patients or biological samples. The following section discusses methods of making and using the medicaments described herein.

Methods of Making and Using Medicaments Comprising Tripeptide Amides

Methods of making and using medicaments comprising the tripeptide amides disclosed herein are also embodiments of the present invention. The tripeptide amides described herein can be processed in accordance with conventional methods of galenic pharmacy to produce medicinal agents for administration to patients, e.g., mammals including humans. The peptide agents can be incorporated into a pharmaceutical product with and without modification. Further, the manufacture of pharmaceuticals or therapeutic agents that deliver the peptide agent by several routes is included within the scope of the present invention.

The compounds described herein can be employed in admixture with conventional excipients, i.e., pharmaceutically acceptable organic or inorganic carrier substances suitable for parenteral, enteral (e.g., oral) or topical application that do not deleteriously react with the peptide agents. Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

In some embodiments, medicaments comprising tripeptide agents are formulated with or administered in conjunction with other agents that inhibit viral infections, such as HIV infection, so as to achieve a better viral response. At present four different classes of drugs are in clinical use in the antiviral treatment of HIV-1 infection in humans. These are (i) nucleoside analogue reverse transcriptase inhibitors (NRTIs), such as zidovidine, lamivudine, stavudine, didanosine, abacavir, and zalcitabine; (ii) nucleotide analogue reverse transcriptase inhibitors, such as adetovir and pivaxir; (iii) non-nucleoside reverse transcriptase inhibitors (NNRTIs), such as efavirenz, nevirapine, and delavirdine; and (iv) protease inhibitors, such as indinavir, nelfinavir, ritonavir, saquinavir and amprenavir. By simultaneously using two, three, or four different classes of drugs in conjunction with administration of the peptide agents, HIV is less likely to develop resistance, since it is less probable that multiple mutations that overcome the different classes of drugs and the peptide agents will appear in the same virus particle.

It is thus preferred that medicaments comprising tripeptide agents be formulated with or given in combination with nucleoside analogue reverse transcriptase inhibitors, nucleotide analogue reverse transcriptase inhibitors, non-nucleoside reverse transcriptase inhibitors, and protease inhibitors at doses and by methods known to those of skill in the art. Medicaments comprising the tripeptide agents and nucleoside analogue reverse transcriptase inhibitors, nucleotide analogue reverse transcriptase inhibitors, non-nucleoside reverse transcriptase inhibitors, and protease inhibitors can be formulated to contain other ingredients to aid in delivery, retention, or stability of the tripeptide amide.

The effective dose and method of administration of a particular tripeptide agent formulation can vary based on the individual patient and the stage of the disease, as well as other factors known to those of skill in the art. Therapeutic efficacy and toxicity of such compounds can be determined by standard pharmaceutical procedures in cell cultures or experimental animals, e.g., $ED_{50}$ and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Normal dosage amounts may vary from approximately 1 to 100,000 micrograms, up to a total dose of about 10 grams, depending upon the route of administration. Desirable dosages include 250 $\mu$g, 500 $\mu$g, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. Additionally, the concentrations of tripeptide agents can be quite high in embodiments that administer the agents in a topical form. Molar concentrations of peptide agents can be used with some embodiments. Desirable concentrations for topical administration and/or for coating medical equipment range from 100 $\mu$M to 800 mM. Preferable concentrations for these embodiments range from 500 $\mu$M to 500 mM. For example, preferred concentrations for use in topical applications and/or for coating medical equipment include 500 $\mu$M, 550 $\mu$M, 600 $\mu$M, 650 $\mu$M, 700 $\mu$M, 750 $\mu$M, 800 $\mu$M, 850 $\mu$M, 900 $\mu$M, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM. Guidance as to particular dosages and methods of delivery is provided in the literature and below. (See e.g., U.S. Pat. Nos. 4,657,760; 5,206,344; or 5,225,212, herein expressly incorporated by reference in their entireties).

More specifically, the dosage of the tripeptide agents described herein is one that provides sufficient tripeptide agent to attain a desirable effect including binding of a capsomere protein, such as p24, and/or interference with capsid assembly and/or inhibition of viral infection, such as HIV and SIV infection. Accordingly, the dose of tripeptide agent preferably produces a tissue or blood concentration or both from approximately 0.1 $\mu$M to 500 $\mu$mM. Desirable doses produce a tissue or blood concentration or both of about 1 to 800 $\mu$M. Preferable doses produce a tissue or blood concentration of greater than about 10 $\mu$M to about 500 $\mu$M. Preferable doses are, for example, the amount of small tripeptide required to achieve a tissue or blood concentration or both of 10 $\mu$M, 15 $\mu$M, 20 $\mu$M, 25 $\mu$M, 30 $\mu$M, 35 $\mu$M, 40 $\mu$M, 45 $\mu$M, 50 $\mu$M, 55 $\mu$M, 60 $\mu$M, 65 $\mu$M, 70 $\mu$M, 75 $\mu$M, 80 $\mu$M, 85 $\mu$M, 90 $\mu$M, 95 $\mu$M, 100 $\mu$M, 110 $\mu$M, 120 $\mu$M, 130 $\mu$M, 140 $\mu$M, 145 $\mu$M, 150 $\mu$M, 160 $\mu$M, 170 $\mu$M, 180 $\mu$M, 190 $\mu$M 200 $\mu$M, 220 $\mu$M, 240 $\mu$M, 250 $\mu$M, 260 $\mu$M, 280 $\mu$M, 300 $\mu$M, 320 $\mu$M, 340 $\mu$M, 360 $\mu$M, 380 $\mu$M, 400 $\mu$M, 420 $\mu$M, 440 $\mu$M, 460 $\mu$M, 480 $\mu$M, and 500 $\mu$M. Although doses that produce a tissue concentration of greater than 800 $\mu$M are not preferred, they can be used with some embodiments. A constant infusion of the tripeptide amide can also be provided so as to maintain a stable concentration in the tissues as measured by blood levels. Higher tissue concentrations can be maintained without harm due to the low toxicity of the tripeptides. Attempts to select small peptide resistant strains of HIV-1 have so far been unsuccessful.

Routes of administration of the tripeptide agents include, but are not limited to, topical, transdermal, parenteral, gastrointestinal, transbronchial, and transalveolar. Topical administration is accomplished via a topically applied cream, gel, rinse, etc. containing a tripeptide. Transdermal administration is accomplished by application of a cream, rinse, gel, etc. capable of allowing the tripeptide agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of tripeptide agent-containing compounds suitable for topical application include, but are not limited to, physiologically acceptable implants, ointments, creams, rinses, and gels. Any liquid, gel, or solid pharmaceutically acceptable base in which the peptides are at least minimally soluble is suitable for topical use in the present invention. Compositions for topical application are particularly useful during sexual intercourse to prevent transmission of HIV. Suitable compositions for such use include, but are not limited to, vaginal or anal suppositories, creams, and douches.

Compositions of the tripeptide agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference and are well known in the art. Examples of suitable transdermal devices are described, for instance, in U.S. Pat. No. 4,818, 540, issued Apr. 4, 1989 to Chinen, et al., hereby incorporated by reference in its entirety.

Compositions of the tripeptide agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the peptide agents.

Compositions of the tripeptide agents suitable for transbronchial and transalveolar administration include, but are not limited to, various types of aerosols for inhalation. For instance, pentamidine is administered intranasally via aerosol to AIDS patients to prevent pneumonia caused by *pneumocystis carinii*. Devices suitable for transbronchial and transalveolar administration of the peptides, including but not limited to atomizers and vaporizers, are also included within the scope of the present invention. Many forms of currently available atomizers and vaporizers can be readily adapted to deliver peptide agents.

Compositions of the tripeptide agents suitable for gastrointestinal administration include, but not limited to, pharmaceutically acceptable powders, pills or liquids for ingestion and suppositories for rectal administration. Due to the most common routes of HIV infection and the ease of use, gastrointestinal administration, particularly oral, is the preferred embodiment of the present invention. Five-hundred milligram capsules having a tripeptide amide have been prepared and were found to be stable for a minimum of 12 months when stored at 4° C. Since small peptides apparently evade degradation by the patient's digestive system, they are ideal for oral administration.

The tripeptide agents are also suitable for use in situations where prevention of HIV infection is important. For instances, medical personnel are constantly exposed to patients who may be HIV positive and whose secretions and body fluids contain the HIV virus. Further, the peptide agents can be formulated into antiviral compositions for use during sexual intercourse so as to prevent transmission of HIV. Such compositions are known in the art and also described in the international application published under the PCT publication number WO90/04390 on May 3, 1990 to Modak et al., which is incorporated herein by reference in its entirety.

Embodiments of the invention also include a coating for medical equipment such as gloves, sheets, and work surfaces that protects against viral transmission. Alternatively, the tripeptide agents can be impregnated into a polymeric medical device. Particularly preferred are coatings for medical gloves and condoms. Coatings suitable for use in medical devices can be provided by a powder containing the peptides or by polymeric coating into which the peptide agents are suspended. Suitable polymeric materials for coatings or devices are those that are physiologically acceptable and through which a therapeutically effective amount of the tripeptide agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al., which is incorporated herein by reference in its entirety.

Accordingly, methods of making a medicament that inhibits viral replication, specifically, HIV, involve providing a tripeptide amide selected from the group consisting of Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$, and formulating said medicament for delivery to a subject, including a human, as described above.

Methods of identification of tripeptide agents that inhibit viral replication, specifically HIV replication, are also provided. By one method, for example, a tripeptide agent for incorporation into an anti-viral pharmaceutical is identified by contacting a plurality of cells infected with a virus with an effective amount of a tripeptide agent, analyzing the virus for incomplete capsid formation, and selecting the tripeptide agent that induces incomplete capsid formation. This method can involve an analysis of capsid formation that employs microscopy and the virus can be selected from the group consisting of HIV-1, HIV-2, and SIV. Further, the peptide agent identified can be selected from the group consisting of a tripeptide amide and a peptidomimetic resembling a tripeptide amide. For example, the peptide agent above can be selected from the group consisting of Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln-NH$_2$, Glu-Gln-Ala-NH$_2$, Val-Lys-Asn-NH$_2$, Thr-Glu-Thr-NH$_2$, Leu-Leu-Val-NH$_2$, Val-Gln-Asn-NH$_2$, Gln-Asn-Ala,-NH$_2$, Asn-Ala-Asn-NH$_2$, Asn-Pro-Asp-NH$_2$, Pro-Asp-Cys-NH$_2$, Cys-Lys-Thr-NH$_2$, Thr-Ile-Leu-NH$_2$, Pro-Gly-Ala-NH$_2$, Thr-Leu-Glu-NH$_2$, Thr-Ala-Cys-NH$_2$, Ala-Cys-Gln-NH$_2$, Gln-Gly-Val-NH$_2$, Pro-Gly-His-NH$_2$, and Arg-Val-Leu-NH$_2$. In a preferred embodiment, the peptide agent used in the method described above has an amino acid sequence that corresponds to an amino acid sequence of p24.

In another embodiment, a method of identifying a peptide agent that binds to a viral protein is provided. Some aspects of this method involve providing a viral protein, contacting the viral protein with an effective amount of a peptide agent, and detecting the formation of a complex comprising the viral protein and the peptide agent. Preferably, the viral protein is from a virus selected from the group consisting of HIV-1, HIV-2, and SIV. The detection step can be accomplished by performing a binding assay (e.g., a p24 binding assay involving dialysis, capillary electrophoresis, computer modeling, or crystallography).

A method of identifying a peptide agent that binds to a viral protein using dialysis can be performed, as follows. Approximately 50 μl of 10 μM solutions of recombinant protein p24, recombinant gp120, or BSA are placed in a 10 kD cut-off dialysis cassette (Slide-A-Lyzer from Pierce) and are dialyzed against 500 ml of buffer containing 150 mM NaCl, 50 mM Tris-HCl, pH 7.4, and 27.5 μM $^{14}$C labeled tripeptide amide at 4° C. for 2 days. Radioactivity can then be quantified in a Rackbeta 1218 (LKB Wallace) after mixing 10 μl or 5 μl of the proteins in ReadySafe (Beckman). Another method of identifying a peptide agent that binds to a viral protein using dialysis can be performed as follows. A piece of fused silica tubing (inner diameter 50 μm) is cut to a length of 23 cm (length to the detector 18.5 cm) and coated prior to use with 5% (w/v) linear polyacrylamide (Hjertén, S. *J. Chromatogr.* 347, 191–198 (1985), expressly incorporated by reference in its entirety) in order to suppress the electroendosmotic flow and to avoid unwanted adsorption of proteins onto the capillary wall. A 0.01 M sodium phosphate solution is used as buffer in the pH range 6.8–8.2. The tripeptide amides are dissolved in the buffer at a relatively high concentration (0.5 mg/ml) because of their low UV-absorbance. A stock solution of p24 is diluted ten-fold with the running buffer to a final concentration of 50 μg/ml. The capillary is filled with the buffer. The protein is injected by pressure (50 psi per second) and then the tripeptide sample (1 psi per second). Since the electrophoretic migration velocity of the peptide is higher than that of the protein, the peptide molecules will move through the protein zone (Hjertén, S. Analysis and purification of cells with the free zone electrophoresis equipment. In *Cell Separation Methods,* Loemendal, H., editor. Elsevier/North-Holland Biomedical Press (1977), expressly incorporated by reference in its entirety). Spectra can be recorded over the whole UV range (195–360 nm with 5 nm frequency) for on tube identification of the peaks. An interaction between the protein and the peptide will be revealed as an increase in migration time of the peptide compared to that in the absence of the protein.

In some embodiments, the tripeptide amide is selected from the group consisting of Ser-Ile-Leu-NH$_2$, Ile-Leu-Asp-NH$_2$, Gly-Pro-Lys-NH$_2$, Pro-Lys-Glu-NH$_2$, Lys-Glu-Pro-NH$_2$, Glu-Pro-Phe-NH$_2$, Arg-Asp-Tyr-NH$_2$, Asp-Tyr-Val-NH$_2$, Tyr-Lys-Thr-NH$_2$, Arg-Ala-Glu-NH$_2$, Ala-Glu-Gln- NH₂, Glu-Gln-Ala-NH₂, Val-Lys-Asn-NH₂, Thr-Glu-Thr-NH₂, Leu-Leu-Val-NH₂, Val-Gln-Asn-NH₂, Gln-Asn-Ala,-NH₂, Asn-Ala-Asn-NH₂, Asn-Pro-Asp-NH₂, Pro-Asp-Cys-NH₂, Cys-Lys-Thr-NH₂, Thr-Ile-Leu-NH₂, Pro-Gly-Ala-NH₂, Thr-Leu-Glu-NH₂, Thr-Ala-Cys-NH₂, Ala-Cys-Gln-NH₂, Gln-Gly-Val-NH₂, Pro-Gly-His-NH₂, and Arg-Val-Leu-NH₂. Additionally, a method of making a pharmaceutical is provided in which the peptide agent identified by the methods above are incorporated in a pharmaceutical.

Another approach to making a pharmaceutical involves administering to a cell an effective amount of a tripeptide amide, described above, detecting an inhibition of viral replication in the cell, and incorporating the tripeptide amide that causes inhibition of viral replication into the pharmaceutical. This method can involve the use of a tripeptide amide selected from the group consisting of Ser-Ile-Leu-NH₂, Ile-Leu-Asp-NH₂, Gly-Pro-Lys-NH₂, Pro-Lys-Glu-NH₂, Lys-Glu-Pro-NH₂, Glu-Pro-Phe-NH₂, Arg-Asp-Tyr-NH₂, Asp-Tyr-Val-NH₂, Tyr-Lys-Thr-NH₂, Arg-Ala-Glu-NH₂, Ala-Glu-Gln-NH₂, Glu-Gln-Ala-NH₂, Val-Lys-Asn-NH₂, Thr-Glu-Thr-NH₂, Leu-Leu-Val-NH₂, Val-Gln-Asn-NH₂, Gln-Asn-Ala,-NH₂, Asn-Ala-Asn-NH₂, Asn-Pro-Asp-NH₂, Pro-Asp-Cys-NH₂, Cys-Lys-Thr-NH₂, Thr-Ile-Leu-NH₂, Pro-Gly-Ala-NH₂, Thr-Leu-Glu-NH₂, Thr-Ala-Cys-NH₂, Ala-Cys-Gln-NH₂, Gln-Gly-Val-NH₂, Pro-Gly-His-NH₂, and Arg-Val-Leu-NH₂. Further, the method above can be supplemented with administration of an antiviral compound selected from the group consisting of nucleoside analogue reverse transcriptase inhibitors, nucleotide analogue reverse transcriptase inhibitors, non-nucleoside reverse transcriptase inhibitors, and protease inhibitors into the pharmaceutical. Additionally, the method above can be supplemented by incorporating a carrier into the pharmaceutical.

Although the tripeptide agents described herein can be used as research tools to analyze the interaction of the tripeptide amide with a protein, desirably they are used to inhibit viral replication and/or infection, preferably, HIV replication and infection in a subject. By one method, for example, a subject at risk of becoming infected by HIV or who is already infected with HIV is identified and said subject is provided a tripeptide amide selected from the group consisting of Ser-Ile-Leu-NH₂, Ile-Leu-Asp-NH₂, Gly-Pro-Lys-NH₂, Pro-Lys-Glu-NH₂, Lys-Glu-Pro-NH₂, Glu-Pro-Phe-NH₂, Arg-Asp-Tyr-NH₂, Asp-Tyr-Val-NH₂, Tyr-Lys-Thr-NH₂, Arg-Ala-Glu-NH₂, Ala-Glu-Gln-NH₂, Glu-Gln-Ala-NH₂, Val-Lys-Asn-NH₂, Thr-Glu-Thr-NH₂, Leu-Leu-Val-NH₂, Val-Gln-Asn-NH₂, Gln-Asn-Ala,-NH₂, Asn-Ala-Asn-NH₂, Asn-Pro-Asp-NH₂, Pro-Asp-Cys-NH₂, Cys-Lys-Thr-NH₂, Thr-Ile-Leu-NH₂, Pro-Gly-Ala-NH₂, Thr-Leu-Glu-NH₂, Thr-Ala-Cys-NH₂, Ala-Cys-Gln-NH₂, Gln-Gly-Val-NH₂, Pro-Gly-His-NH₂, and Arg-Val-Leu-NH₂. By an additional method, a subject is provided a tripeptide amide selected from the group consisting of Ser-Ile-Leu-NH₂, Ile-Leu-Asp-NH₂, Gly-Pro-Lys-NH₂, Pro-Lys-Glu-NH₂, Lys-Glu-Pro-NH₂, Glu-Pro-Phe-NH₂, Arg-Asp-Tyr-NH₂, Asp-Tyr-Val-NH₂, Tyr-Lys-Thr-NH₂, Arg-Ala-Glu-NH₂, Ala-Glu-Gln-NH₂, Glu-Gln-Ala-NH₂, Val-Lys-Asn-NH₂, Thr-Glu-Thr-NH₂, Leu-Leu-Val-NH₂, Val-Gln-Asn-NH₂, Gln-Asn-Ala,-NH₂, Asn-Ala-Asn-NH₂, Asn-Pro-Asp-NH₂, Pro-Asp-Cys-NH₂, Cys-Lys-Thr-NH₂, Thr-Ile-Leu-NH₂, Pro-Gly-Ala-NH₂, Thr-Leu-Glu-NH₂, Thr-Ala-Cys-NH₂, Ala-Cys-Gln-NH₂, Gln-Gly-Val-NH₂, Pro-Gly-His-NH₂, and Arg-Val-Leu-NH₂ and the effect on viral replication or infection, preferably HIV replication or infection, is determined (e.g., by analyzing the amount of p24 or reverse transcriptase activity in a sample).

The methods above can be supplemented with administration of an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the tripeptide amide used in these methods can be joined to a support or can be administered in a pharmaceutical comprising a pharmaceutically acceptable carrier.

While the present invention has been described in some detail for purposes of clarity and understanding, one skilled in the art will appreciate that various changes in form and detail can be made without-departing from the true scope of the invention. All figures and tables, as well as patents, applications, and publications referred to above are hereby expressly incorporated by reference in their entireties.

What is claimed is:

1. A composition comprising PRO-LYS-GLU-NH$_2$.

2. A pharmaceutical composition comprising PRO-LYS-GLU-NH$_2$.

3. A tripeptide amide consisting of PRO-LYS-GLU-NH$_2$.

4. The tripeptide amide of claim 3, further comprising a support.

5. The tripeptide amide of claim 3, further comprising a pharmaceutically acceptable carrier.

* * * * *